(12) United States Patent
Kronenberger

(10) Patent No.: US 11,110,221 B2
(45) Date of Patent: Sep. 7, 2021

(54) SYSTEM AND METHOD FOR MANAGING ADMINISTRATION OF INSULIN TO A USER

(71) Applicant: Robert Kronenberger, Deerfield, IL (US)

(72) Inventor: Robert Kronenberger, Deerfield, IL (US)

( * ) Notice: Subject to any disclaimer, the term of this patent is extended or adjusted under 35 U.S.C. 154(b) by 0 days.

(21) Appl. No.: 15/675,918

(22) Filed: Aug. 14, 2017

(65) Prior Publication Data

US 2019/0046722 A1 Feb. 14, 2019

(51) Int. Cl.
| | |
|---|---|
| *A61M 5/172* | (2006.01) |
| *A61M 5/142* | (2006.01) |
| *G16H 50/20* | (2018.01) |
| *G16H 20/10* | (2018.01) |

(52) U.S. Cl.
CPC .......... *A61M 5/1723* (2013.01); *A61M 5/142* (2013.01); *G16H 20/10* (2018.01); *G16H 50/20* (2018.01); *A61M 2005/14208* (2013.01); *A61M 2005/1726* (2013.01); *A61M 2202/04* (2013.01); *A61M 2205/3592* (2013.01); *A61M 2230/201* (2013.01)

(58) Field of Classification Search
CPC ................ A61M 5/1723; A61M 5/142; A61M 2005/14208; A61M 2005/1726; A61M 2230/201; A61M 2204/04; G06F 19/3468; G16H 50/20; G16H 20/10
See application file for complete search history.

(56) References Cited

U.S. PATENT DOCUMENTS

| | | | | |
|---|---|---|---|---|
| 2005/0245878 | A1* | 11/2005 | Mernoe | G16H 20/17 604/180 |
| 2008/0172029 | A1* | 7/2008 | Blomquist | G06F 19/00 604/500 |
| 2009/0209938 | A1* | 8/2009 | Aalto-Setala | A61B 5/02438 604/503 |
| 2009/0254037 | A1* | 10/2009 | Bryant, Jr. | A61M 5/142 604/151 |
| 2012/0277716 | A1* | 11/2012 | Ali | G06F 19/3468 604/500 |
| 2013/0338629 | A1* | 12/2013 | Agrawal | A61M 5/1723 604/504 |
| 2014/0039383 | A1* | 2/2014 | Dobbles | G06F 19/00 604/66 |

\* cited by examiner

*Primary Examiner* — James D Ponton
(74) *Attorney, Agent, or Firm* — Wood, Phillips, Katz, Clark & Mortimer

(57) ABSTRACT

A system for managing administration of insulin to a user includes an infusion pump to effect controlled delivery of insulin A user interface device displays representations of user intake items. A database stores a catalog of intake items. A programmed processing system is programmed with a baseline user insulin delivery program to make a calculation of insulin to be delivered according to the baseline insulin delivery program or according to a modified baseline insulin delivery program based upon user input data. The user provides user input using the user interface application to identify representations of any of the plurality of intake items and the processing system automatically effects delivery of insulin to the user according to the modified baseline insulin delivery program, instead of the baseline insulin delivery program.

16 Claims, 1 Drawing Sheet

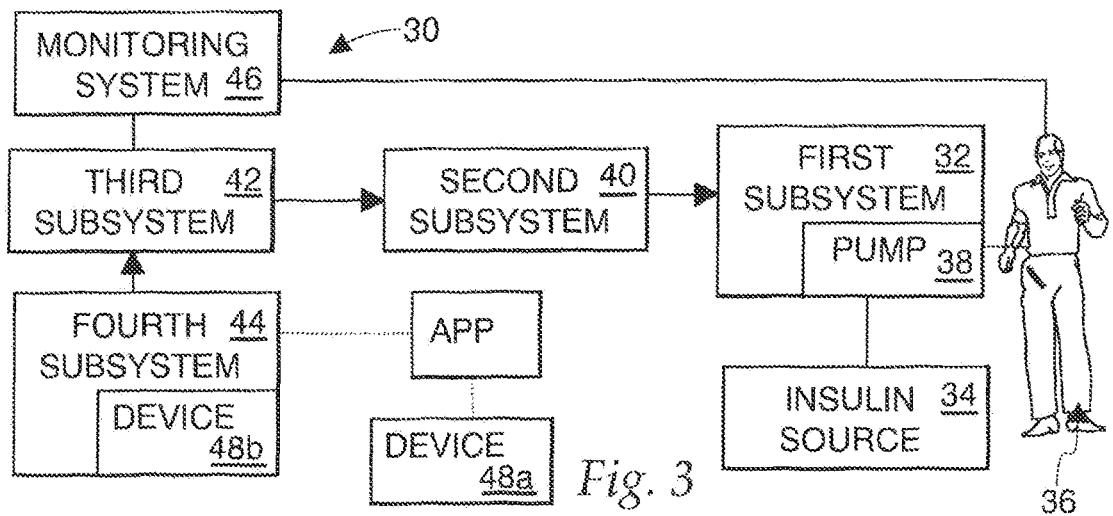
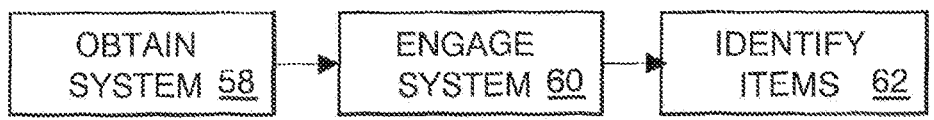
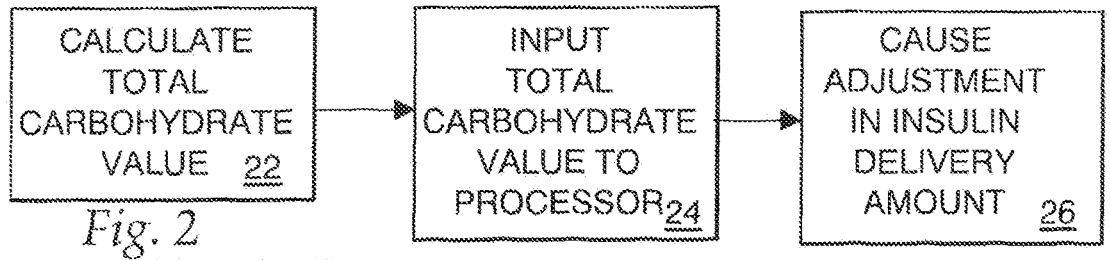
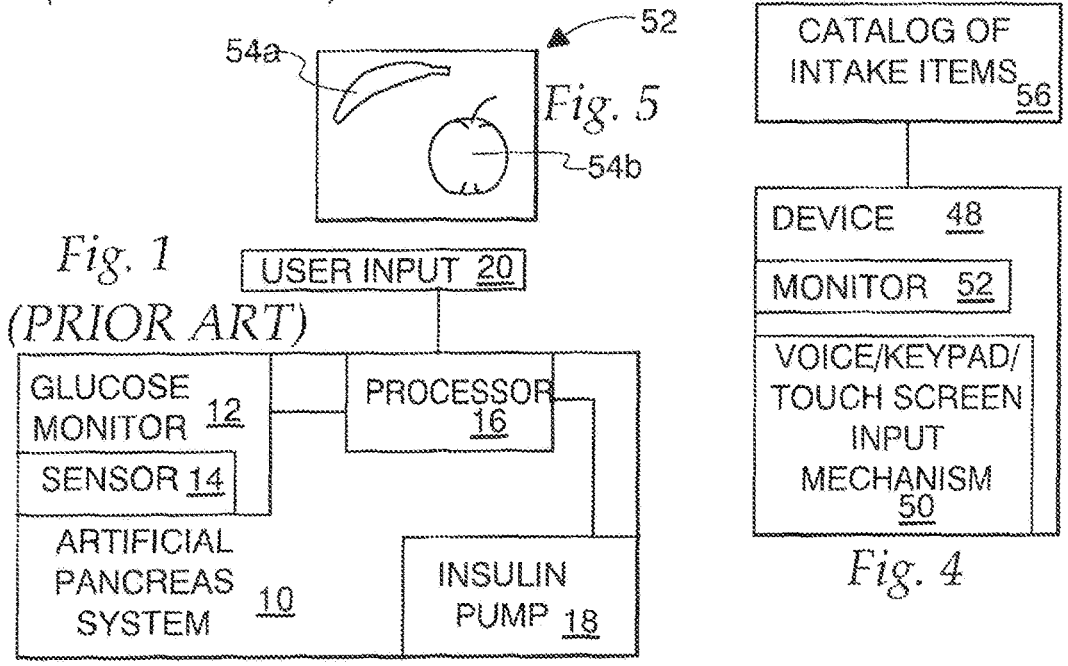

SYSTEM AND METHOD FOR MANAGING ADMINISTRATION OF INSULIN TO A USER

BACKGROUND OF THE INVENTION

Field of the Invention

This invention relates to systems for controllably delivering insulin to a user with a diabetic condition and, more particularly, to a system wherein a user inputs information related to his/her activities that control the delivered insulin amount.

Background Art

A diabetic condition occurs when the pancreas produces inadequate amounts of insulin needed to regulate blood glucose. Type 1 diabetes is a condition that results when the pancreas produces either no insulin or limited quantities of insulin that are inadequate to regulate blood glucose. Type 2 diabetes is a condition that results when the pancreas produces a greater amount of insulin but still an amount that is inadequate to regulate blood glucose. Type 2 diabetes may also be a result of the body rejecting the produced insulin.

Insulin infusion therapy has been practiced by those with both Type 1 and Type 2 diabetic conditions for decades. Controlled doses of insulin are injected to regulate blood glucose.

A common treatment practice requires that an individual test his/her blood glucose level using any number of available meters. The identified glucose level at time of testing dictates the dose of insulin to be administered. The administration may be effected through a needle or through an insulin infusion pump.

Continuous glucose monitoring systems are also available to facilitate self-administration of insulin.

Another level of sophistication has been built into artificial pancreas systems. While these systems vary in terms of their sophistication and cost, they generally operate using the same basic components/systems.

A glucose monitor continuously measures glucose level. This monitoring may be effected by strategically placing a sensor subcutaneously within cells in fluid reflecting blood glucose levels. Various electronic devices have been devised to generate signals representative of a particular glucose level as well as potentially the trending of levels determined based upon the continuous monitoring.

A processor receives a signal from the glucose monitor and performs calculations that identify an appropriate amount of insulin to be infused.

The signal from the processor causes activation of an infusion pump which delivers the predetermined amount of insulin to under the individual's skin.

Artificial pancreas systems are also designed so that they will change insulin delivery based upon periodic inputs from the individual. This is critical since glucose levels are affected by the individual's anatomy as well as lifestyle, to include activity levels, diet, etc.

For example, artificial pancreas systems are commonly constructed so that they will adjust insulin dosage in response to a user input with respect to what an individual consumes throughout the day.

Intake of carbohydrates is critical in the monitoring of blood glucose levels. Even if the system is capable of continuous monitoring, an infusion of carbohydrates or other type of food product may cause a momentary significant change in blood glucose level. A delay in detecting this change in blood glucose level could have detrimental effects. Thus, current systems commonly are configured to allow a user to input information regarding consumed foods that will change the calculations that dictate the insulin dose administered so that a preemptive change in an insulin dosage can be made.

Heretofore, systems have been devised to accept, for example, a total for carbohydrate consumption. Individuals may become familiar with how many carbohydrates are in a particular food product, whereby they might input the carbohydrate amount to the controller. In anticipation of a full meal, an individual has to identify all food products to be consumed, calculate the carbohydrates associated with each, and input the total for a given meal. This may require the individual to research the carbohydrate content of many different food types, including many for which the carbohydrate amount may not be readily identifiable. Thus, the total carbohydrate quantity submitted may end up being only a rough estimate, with certain food articles ignored in the calculation or their carbohydrate content only grossly estimated.

Even if sophisticated systems are ultimately devised that will rapidly identify changing glucose levels following food consumption, an unavoidable lag in computations results which could have significant effects on the individual. The complicated manner in which carbohydrate totals and the like are required to be currently calculated inevitably leads to infusion of insulin that is not optimal.

In spite of the above limitations, the industry has yet to devise a system that is user friendly and allows accurate input of information relating to consumed articles to permit system adjustment for appropriate infusion of an insulin dosage.

SUMMARY OF THE INVENTION

In one form, the invention is directed to a system for managing administration of insulin to a user. The system includes: a first subsystem configured to effect a controlled delivery of insulin from a source to a user; a second subsystem configured to generate an input to the first subsystem to cause the first subsystem to effect insulin delivery; a third subsystem configured to: a) be programmed with a baseline insulin delivery program for a user; and b) make a calculation of insulin to be delivered to the user according to the baseline insulin delivery program or according to a modified baseline insulin delivery program generated in response to user input data; and a fourth subsystem configured to receive and process input data related to a user's nutritional intake and communicate the user input data derived from the user's nutritional intake to the third subsystem for processing by the third subsystem to allow the third subsystem to modify the baseline delivery program and communicate an input to the second subsystem correlated to the modified baseline insulin delivery program. The second subsystem is configured to process the input from the third subsystem and cause the first subsystem to effect insulin delivery in a manner consistent with the modified baseline insulin delivery program. The fourth subsystem has a database of information with a pre-established relationship between each of a plurality of intake items and a parameter that is related thereto and is usable to determine an appropriate change in insulin delivery based upon the consumption of each of the plurality of intake items. The system is configured to allow the user to provide an input to selectively identify any of the plurality of intake items as an incident of which the related parameters are communicated by one or more inputs to the third subsystem. As an incident of the user inputting an identification of one or more of the intake items, the system is configured to automatically effect delivery of insulin to the user according to the modified baseline delivery program determined by the user's consumption of the one or more of the intake items.

In one form, the parameter is the quantity of one or more compounds in each of the intake items.

In one form, one of the compounds is a carbohydrate.

In one form, the system further includes a device through which the user input to identify the plurality of intake items is generated. The device is a dedicated device.

In one form, the device is a non-dedicated, mobile device.

In one form, the mobile device is a cellular phone that is integrated with the system through a computing application/app.

In one form, the device is configured to generate the user input to identify the plurality of intake items in response to a key pad entry by the user.

In one form, the device is configured to generate the user input to identify the plurality of intake items in response to a voice input from the user.

In one form, the fourth subsystem is configured to process carbohydrates in different intake items differently and based upon criteria other than a total carbohydrate amount in arriving at the modified baseline insulin delivery program.

In one form, the system further includes a device through which the user input to identify the plurality of intake items is generated. The device has a touch screen.

In one form, the device is configured to provide pictorial representation of intake items. The device is further configured so that the user input to identify the plurality of intake items can be generated by contacting the touch screen where the pictorial representations of the intake items reside.

In one form, the device has a catalogued listing of intake items with the related parameters that can be searched through the device.

In one form, the invention further includes a system for monitoring the user's glucose level.

In one form, a system is provided for continuously monitoring a user's glucose level.

In one form, the invention is directed to a method of managing administration of insulin to a user. The method includes the steps of: obtaining the system described above; operatively engaging the system so that the monitoring system can continuously monitor the user's glucose level and the first system can deliver insulin to the user; and either: a) in anticipation of consuming certain intake items; or b) upon consuming certain intake items, providing to the system the identity of each of the certain intake items to thereby cause the related parameters to be communicated to the third subsystem.

In one form, the related parameters are a total amount of carbohydrates in each of the certain intake items.

In one form, the step of providing to the system the identity of each of the certain intake items consists of providing to the system the identity of each of the certain intake items through a mobile device.

BRIEF DESCRIPTION OF THE DRAWINGS

FIG. 1 is a schematic representation of a conventional artificial pancreas system;

FIG. 2 is a flow diagram representation showing a conventional method of managing administration of insulin to a user;

FIG. 3 is a schematic representation of the inventive system for managing administration of insulin to a user;

FIG. 4 is a schematic representation of a device that is part of, or usable with, the system in FIG. 3 through which the user inputs certain information relating to intake items;

FIG. 5 is a front elevation view of a monitor that can be used on the device as shown in FIG. 4 with pictorial representations of intake items; and FIG. 6 is a flow diagram representation of a method of managing administration of insulin using the system in FIG. 1.

DETAILED DESCRIPTION OF THE PREFERRED EMBODIMENT

In FIG. 1, a conventional artificial pancreas system is shown schematically at 10. The artificial pancreas system 10 consists of a glucose monitor 12 capable of continuously monitoring a user's glucose level.

The glucose monitor 12 measures glucose level through a sensor 14. Many types of sensor 14 currently exist.

The glucose monitor 12 causes an input, representative of the glucose level, to a processor 16. The processor 16 may include a software embedded algorithm that performs calculations, based upon which a dosing instruction is input to an insulin pump 18.

The control algorithm can be run on any of a number of different devices, among which may be the insulin pump 18 itself, a computer, a cellular phone, etc.

The processor 16 is also capable of receiving a user input 20 through an appropriate device that may be part of the artificial pancreas system 10, or separately linked thereto.

Processors 16 are typically designed to receive a total carbohydrate value, based upon the individual's consumption, through the user input 20. This may be a single numerical amount that is determined by the individual as through the steps shown in flow diagram form in FIG. 2.

More specifically, in anticipation of consuming, or upon consuming, certain food articles, the individual equates each consumed food article with a carbohydrate number and combines all numbers for all of the consumed articles to calculate a total carbohydrate value, as shown at block 22.

As shown at block 24, the total carbohydrate value is input to the processor 16 on the artificial pancreas system 10.

As shown at block 26, the input in block 24 causes the processor to effect an adjustment in insulin delivery amount through the insulin pump 18.

In FIG. 3, a system for managing administration of insulin to a user, according to the invention, is shown in schematic form at 30.

The system 30 consists of a first subsystem 32 configured to effect a controlled delivery of insulin from an insulin source 34 to a user 36 through conventional delivery means. Typically; the means will include a pump 38.

A second subsystem 40 is configured to generate an input to the first subsystem 32 to cause the first subsystem 32 to effect insulin delivery.

A third subsystem 42 is configured to: a) be programmed with a baseline insulin delivery program for a user; and b) make a calculation of insulin to be delivered to the user according to the baseline insulin delivery program or according to a modified baseline insulin delivery program generated in response to input user data.

A fourth subsystem 44 is configured to receive and process data related to a user's nutritional intake and communicate the input user data derived from the user's nutritional intake to the third subsystem 42 for processing by the third subsystem. This input causes the third subsystem 42 to modify the baseline delivery program and communicate an input to the second subsystem 40 correlated to the modified baseline insulin delivery program.

The second subsystem 40 is configured to process the input from the third subsystem 42 and cause the first subsystem 32 to effect insulin delivery in a manner consistent with the modified baseline insulin delivery program.

The fourth subsystem 44 has a database of information with pre-established relationships between each of a plurality of intake items and a parameter that is related thereto and usable to determine an appropriate change in insulin delivery based upon consumption of each of the plurality of intake items. The system 30 is configured to allow the user to provide an input to selectively identify any of the plurality of intake items, as an incident of which the related parameters are communicated by one or more inputs to the fourth subsystem 44. The system 30 is configured so that as an incident of the user inputting an identification of one or more of the intake items, the system 30 automatically effects delivery of insulin to the user according to the modified baseline program determined by taking into account the user's consumption of the one or more of the intake items.

Typically, the parameter will be the quantity of one or more compounds in each of the intake items. Commonly, the tracked compound is a carbohydrate. As an example, the user, in anticipation of eating an apple and a banana, may input the identification of these intake items, as an incident of which the total carbohydrates will be automatically determined and a representative signal sent to the third subsystem 42.

A monitoring system 46 is provided to monitor the user's glucose level. The monitoring system 46 may be one that takes measurements at different set or selected times or one that continuously monitors a user's glucose level.

A device 48a, 48b is provided through which the user input, to identify the plurality of intake items, is generated. The device 48b is shown as a dedicated device that is part of the fourth subsystem 44.

The device 48a is a non-dedicated device and may be, for example, a mobile device, such as a computer or cellular phone.

In the case of a cellular phone, integration of the device 48a into the system 10 may be effected through a computing application/app.

As shown in FIG. 4, the device 48 (48a or 48b) may be configured so that the user input mechanism 50 is one of a touch screen, a keypad, a voice responsive input device, etc.

The device 48 may have a monitor 52 to facilitate operation. As shown in FIG. 5, the monitor 52 may have pictorial representations of intake items. In FIG. 5, pictorial representations 54a, 54b are shown for a banana and an apple, respectively. With a touch screen capability, a user might simply scroll to a page with a desired pictorial representation corresponding to the intake item and touch the monitor 52 to effect the input to the system 30.

As shown in FIG. 4, the device 48, or another part of the system 30, may have a catalogue of intake items 56 that might be searched to facilitate a quick and simple input related to the particular intake item to be consumed.

The fourth subsystem 44 may be configured to process carbohydrates in different food items differently, and based upon criteria other than a total carbohydrate amount, in arriving at the modified baseline insulin delivery program. There are different types of carbohydrates that are assimilated differently into the body and that affect glucose levels in different manners. This feature adds another level of accuracy to the insulin dosage selection.

With the system 30 as described above, a method of managing administration of insulin to a user can be performed as shown in flow diagram form in FIG. 6.

As shown at block 58, the above system is obtained.

As shown at block 60, the user engages him/herself operatively with the system.

As shown at block 62, in anticipation of consuming certain intake items, or upon consuming certain intake items, the user provides the identity of each of the certain items to thereby cause the related parameters to be communicated to the fourth subsystem.

The foregoing disclosure of specific embodiments is intended to be illustrative of the broad concepts comprehended by the invention.

The invention claimed is:

1. A system for continuously monitoring a user's glucose level and automatically managing administration of insulin to the user, the system comprising:
a glucose monitor for continuously monitoring and determining the user's glucose level;
a user interface device operating a user interface application for displaying representations of user intake items;
a database storing a catalog of input items for display on the user interface application and information with a pre-established relationship between each of a plurality of intake items and a parameter that is related thereto and usable to determine an appropriate change in insulin delivery based upon consumption by the user of each of the plurality of intake items;
an infusion pump configured to effect a controlled delivery of insulin from a source to the user; and
a programmed processing system operatively associated with the glucose monitor, the user interface device, the database and the infusion pump, the programmed processing system being programmed with a baseline insulin delivery program for the user based upon continuously determined glucose levels to calculate insulin to be delivered to the user according to the baseline insulin delivery program and communicate a pump input to the infusion pump correlated to the baseline insulin delivery program to effect insulin delivery in a manner consistent with the baseline insulin delivery program,
the programmed processing system being programmed to allow the user to provide user input using the user interface application to selectively identify representations of any of the plurality of intake items as an incident of which the related parameters are communicated from the database for processing by the processing system to modify the baseline delivery program and communicate a pump input to the infusion pump correlated to the modified baseline insulin delivery program to effect insulin delivery in a manner consistent with the modified baseline insulin delivery program,
whereby as an incident of the user inputting an identification of one or more of the intake items using the user interface application, the system automatically effects delivery of insulin to the user according to the modified baseline insulin delivery program, instead of the baseline insulin delivery program, determined by the user's consumption of the one or more of the plurality of intake items based upon the pre-established relationship in the database of the inputted identification of the one or more of the intake items and the parameter.

2. The system for continuously monitoring a user's glucose level and automatically managing administration of insulin to the user according to claim 1 wherein the parameter is a quantity of one or more compounds in each of the plurality of intake items.

3. The system for continuously monitoring a user's glucose level and automatically managing administration of insulin to the user according to claim 2 wherein one of the one or more of the compounds is a carbohydrate.

4. The system for continuously monitoring a user's glucose level and automatically managing administration of insulin to the user according to claim 3 wherein the programmed processing system is configured to process carbohydrates based upon criteria other than a total carbohydrate amount in arriving at the modified baseline insulin delivery program.

5. The system for continuously monitoring a user's glucose level and automatically managing administration of insulin to the user according to claim 1 wherein the user interface device is a dedicated device.

6. The system for continuously monitoring a user's glucose level and automatically managing administration of insulin to the user according to claim 5 wherein the user interface device is configured to process the user input to identify the plurality of intake items in response to a key pad entry by the user.

7. The system for continuously monitoring a user's glucose level and automatically managing administration of insulin to the user according to claim 5 wherein the user interface device is configured to process the user input to identify the plurality of intake items in response to a voice input from the user.

8. The system for continuously monitoring a user's glucose level and automatically managing administration of insulin to the user according to claim 1 wherein the user interface device is a non-dedicated, mobile device.

9. The system for continuously monitoring a user's glucose level and automatically managing administration of insulin to the user according to claim 8 wherein the mobile device is a cellular phone that is integrated with the system through the user interface application.

10. The system for continuously monitoring a user's glucose level and automatically managing administration of insulin to the user according to claim 1 wherein the user interface device has a touch screen through which the user input is effected.

11. The system for continuously monitoring a user's glucose level and automatically managing administration of insulin to the user according to claim 10 wherein the user interface device is configured to provide pictorial representation of the plurality of intake items and the user interface device is further configured so that the user input to identify the plurality of intake items can be generated by contacting the touch screen where the pictorial representations of the intake items reside.

12. The system for continuously monitoring a user's glucose level and automatically managing administration of insulin to the user according to claim 10 wherein the user interface device has a catalogued listing of the plurality of intake items with the related parameters that can be searched through the user interface device.

13. A method of continuously monitoring a user's glucose level and automatically managing administration of insulin to the user, the method comprising the steps of:
obtaining the system for continuous monitoring of claim 1;
operatively engaging the system for continuous monitoring with the user; and
while the user's glucose level is being continuously monitored, either: a) in anticipation of consuming certain intake items of the plurality of intake items; or b) upon consuming certain intake items of the plurality of intake items, providing to the system for continuous monitoring the identity of each of the certain intake items of the plurality of intake items to thereby cause the related parameters to be communicated to the programed processing system.

14. The method of continuously monitoring a user's glucose level and automatically managing administration of insulin to the user according to claim 13 wherein the related parameters are a total amount of carbohydrates in each of the certain intake items of the plurality of intake items.

15. The method of continuously monitoring a user's glucose level and automatically managing administration of insulin to the user according to claim 13 wherein the step of providing to the system the identity of each of the certain intake items of the plurality of intake items comprises providing to the system for continuous monitoring the identity of each of the certain intake items through a mobile device comprising the user interface device.

16. A method of managing administration of insulin to a user, the method comprising:
providing a system for continuously monitoring the user's glucose level comprising:
a glucose monitor for continuously monitoring and determining the user's glucose level;
a user interface device operating a user interface application for displaying representations of user intake items;
a database storing a catalog of input items for display on the user interface application and information with a pre-established relationship between each of a plurality of the intake items and a parameter that is related thereto and usable to determine an appropriate change in insulin delivery based upon consumption by the user of each of the plurality of intake items;
an infusion pump configured to effect a controlled delivery of insulin from a source to the user; and
a programmed processing system operatively associated with the glucose monitor, the user interface device, the database and the infusion pump and programmed with a baseline insulin delivery program for the user based upon continuously determined glucose levels;
the programmed processing system being programmed to automatically make a calculation of insulin to be delivered to the user according to the baseline insulin delivery program or make the calculation of insulin to be delivered to the user according to a modified baseline insulin delivery program generated in response to user input data; and
the programmed processing system being programmed to allow the user to provide an input using the user interface application to selectively identify representations of any of the plurality of intake items as an incident of which the related parameters are communicated from the database for processing by the processing system to modify the baseline delivery program and communicate an input to the infusion pump correlated to the modified baseline insulin delivery program to effect insulin delivery in a manner consistent with the modified baseline insulin delivery program, whereby as an incident of the user inputting an identification of one or more of the intake items using the user interface application, the system is programmed to automatically effect delivery of insulin to the user according to the modified baseline delivery program, instead of the baseline insulin delivery program, determined by the user's consumption of the one or more of the plurality of intake items based upon the pre-established relationship in the database of the inputted identification of the one or more of the intake items and the parameter.

\* \* \* \* \*